United States Patent [19]

Green

[11] Patent Number: 4,804,274

[45] Date of Patent: Feb. 14, 1989

[54] METHOD AND APPARATUS FOR DETERMINING PHASE TRANSITION TEMPERATURE USING LASER ATTENUATION

[75] Inventor: Gary J. Green, Yardley, Pa.

[73] Assignee: Mobil Oil Corporation, New York, N.Y.

[21] Appl. No.: 947,927

[22] Filed: Dec. 30, 1986

[51] Int. Cl.⁴ .................. G01N 25/04; G01N 25/12
[52] U.S. Cl. .............................. 374/17; 374/25; 374/16
[58] Field of Search ............... 374/16, 17, 25; 356/436; 250/573

[56] References Cited

U.S. PATENT DOCUMENTS

| | | | |
|---|---|---|---|
| 3,412,599 | 11/1968 | Hammons et al. | 374/17 |
| 3,457,772 | 7/1969 | Chassaone et al. | 374/17 |
| 3,545,254 | 12/1970 | Chassaone et al. | 374/17 |
| 3,632,210 | 1/1972 | Rich | 374/17 |
| 3,982,420 | 9/1976 | Blevins et al. | 374/17 |
| 4,171,909 | 10/1979 | Kramer et al. | 356/436 |
| 4,198,767 | 4/1980 | MacPherson et al. | 434/21 |
| 4,519,717 | 5/1985 | Jones et al. | 374/17 |
| 4,549,809 | 10/1985 | Minekane et al. | 356/436 |
| 4,572,676 | 2/1986 | Biermans | 374/17 |
| 4,655,349 | 4/1987 | Joseph et al. | 250/563 |

FOREIGN PATENT DOCUMENTS

| | | | |
|---|---|---|---|
| 0024631 | 2/1980 | Japan | 374/17 |
| 0851351 | 7/1981 | U.S.S.R. | 374/17 |
| 0719259 | 3/1982 | U.S.S.R. | 374/16 |

Primary Examiner—William A. Cuchlinski, Jr.
Assistant Examiner—Thomas B. Will
Attorney, Agent, or Firm—Alexander J. McKillop; Charles J. Speciale

[57] ABSTRACT

Disclosed are methods and apparatus for determining phase transition temperatures and, more particularly, for determining cloud, fluidity, freezing, and haze points of hydrocarbon fuels and hydrocarbon/oxygenate fuel blends. The attenuation of laser light as it passes through the sample, then through a laser line filter, and then into a photodetector is used to determine the transition temperature.

24 Claims, 2 Drawing Sheets

METHOD AND APPARATUS FOR DETERMINING PHASE TRANSITION TEMPERATURE USING LASER ATTENUATION

BACKGROUND OF THE INVENTION

The present invention relates to the determination of phase transition temperatures and, more particularly, to the determination of cloud, fluidity, freezing, and haze points of hydrocarbon fuels and hydrocarbon/oxygenate fuel blends.

Liquid hydrocarbon fuels are characterized by changes in physical form which are critical to its performance and which occur at certain temperatures. The temperatures at which these changes occur are known as "phase transition temperatures" and are commonly used as specifications for hydrocarbon fuels. In general, these phase transitions are defined by the occurrence of visibly observable changes. For example, the cloud point is the temperature at which wax or other insoluble substances begin to crystallize in or separate from a hydrocarbon fuel which has been chilled. Another example of a phase transition temperature which is important in assessing hydrocarbon fuels is "haze point" or "water tolerance test" for gasolines which contain oxygenated octane boosters, such as methanol and/or methyl tertiary-butyl ether (MTBE), in the presence of trace amounts of water. Such measurements are critical for assessing the optimal blending concentration of such oxygenates in gasoline so as to prevent phase separation in fuel tanks and other fuel systems. The separation of these octane boosters from the gasoline phase can have serious deleterious effects on the fuel tanks in which they are stored and on the fuel systems in which they are used. For example, it has been found that methanol may cause deterioration of certain seals and gasket materials currently used in underground storage tanks.

Techniques for determining phase transition temperatures in liquid hydrocarbon fuels have heretofore generally relied upon visual observation by an operator and the subsequent manual recording of the temperature as read from a thermometer. Methods such as ASTM D-2386 (for determining the freezing point of aviation fuels or fluidity point of heating oils and diesel fuels), ASTM D-2500 (for determining the cloud point of petroleum fuels), and the ASTM recommended procedure for determining water tolerance in gasohol are all based on such methodology. While such techniques are generally convenient and inexpensive, they are time consuming and subject to inconsistent visual observation by one or more operators. In addition, the accuracy of such techniques may be greatly influenced by ambient lighting conditions.

Somewhat more sophisticated means for detecting the cloud point of a liquid are currently available. For example, if the cloud point is due to the appearance of crystals having an anisotropic structure, the cloud point may be determined by illuminating the suitably cooled liquid with polarized light. Polarized light, which is normally extinguished in the absence of anisotropic crystals, increases in intensity as it traverses the liquid, this increase being due to the depolarization of the incident rays of light by the appearance of anisotropic crystals. See for example U.S. Pat. No. 3,457,772-Chassagne et al. The apparatus used according to such technique comprises two cells, one a measuring cell designed to receive a liquid to be examined, the other a reference cell. This technique has the disadvantage of being applicable only to liquids having a phase transition which is associated with the appearance of anisotropic crystals.

Another apparatus which may be used for cloud point determination comprises relatively complex and precisely configured primary and secondary light guides positioned so as to project a beam of light from the primary to the secondary light guide via a sample gap. A sensor is provided for responding to a decrease in the intensity of the light emerging from the secondary light guide. See for example U.S. Pat. No. 3,527,082-Pruvot. In order to allow for fluctuations in the intensity of the illumination, primary and secondary photoconductive cells are required in this method. One further disadvantage of this technique is that it requires the balancing of the light intensities at the two photoconductive cells both before use and from time to time as may be necessary during service.

Attempts have been made to overcome the disadvantages of the apparatus and techniques described above by utilizing laser light in place of incandescent lamps. See for example U.S. Pat. No. 3,807,865-Gordon et al. The technique of Gordon et al. uses a relatively complex series of thermal pulses and the measurement of the resultant physical variable changes to determine spinodals and critical points. The use of laser light in the method of Gordon has not reduced the sensitivity of the measuring apparatus to ambient lighting conditions or provided a more compact apparatus.

It has long been desired in many applications to determine phase transition temperatures using a simple and compact apparatus which is not effected by ambient light. For example, a portable and effective cloud point detector would be extremely useful in an industrial setting requiring infrequent but periodic determinations of phase transition temperatures at different locations. Since the ambient conditions at such locations may vary greatly, it is desired for such an apparatus to be both relatively compact and also insensitive to ambient light. Prior apparatus have addressed the problem of ambient light sensitivity by providing light tight housings. See for example U.S. Pat. No. 4,572,676-Biermans. However, such housings are generally expensive; not conducive to the compact nature required of the portable device; and prone to light leaks, especially in the harsh environment of industrial applications.

SUMMARY OF THE INVENTION

It is an object of the present invention to provide accurate methods and apparatus for determining phase transition temperatures in liquids, especially liquid hydrocarbon fuels.

It is another object of the present invention to achieve such accurate determinations in a minimum period of time and with a minimum amount of operator interaction.

It is a still further object to provide such measuring apparatus in a compact form.

It is still another object of the present invention to provide methods and apparatus which are unaffected by ambient lighting conditions.

These and other objects of the present invention are achieved by providing an apparatus for determining the phase transition temperature of a sample comprising: a container for holding the sample having an optical pathway therethrough; means for projecting a highly parallel beam of monochromatic visible light along the optical pathway; means for detecting the intensity of said light exiting the optical pathway; and means for measuring the temperature of the sample.

One embodiment of the present invention for determining the phase transition temperature of a sample comprises: projecting a highly parallel beam of monochromatic visible light along an optical pathway in the sample; measuring the temperature of the sample; and causing the temperature of the sample to pass through the phase transition temperature while simultaneously detecting the intensity of said light exiting said optical pathway, whereby a reduction in the detected intensity of said light is indicative of the occurrence of said phase transition.

DETAILED DESCRIPTION OF THE INVENTION

Apparatus in accordance with preferred embodiments of the present invention will be discussed in greater detail in terms of the specific, non-limiting embodiment illustrated in FIG. 1.

Figure 1:
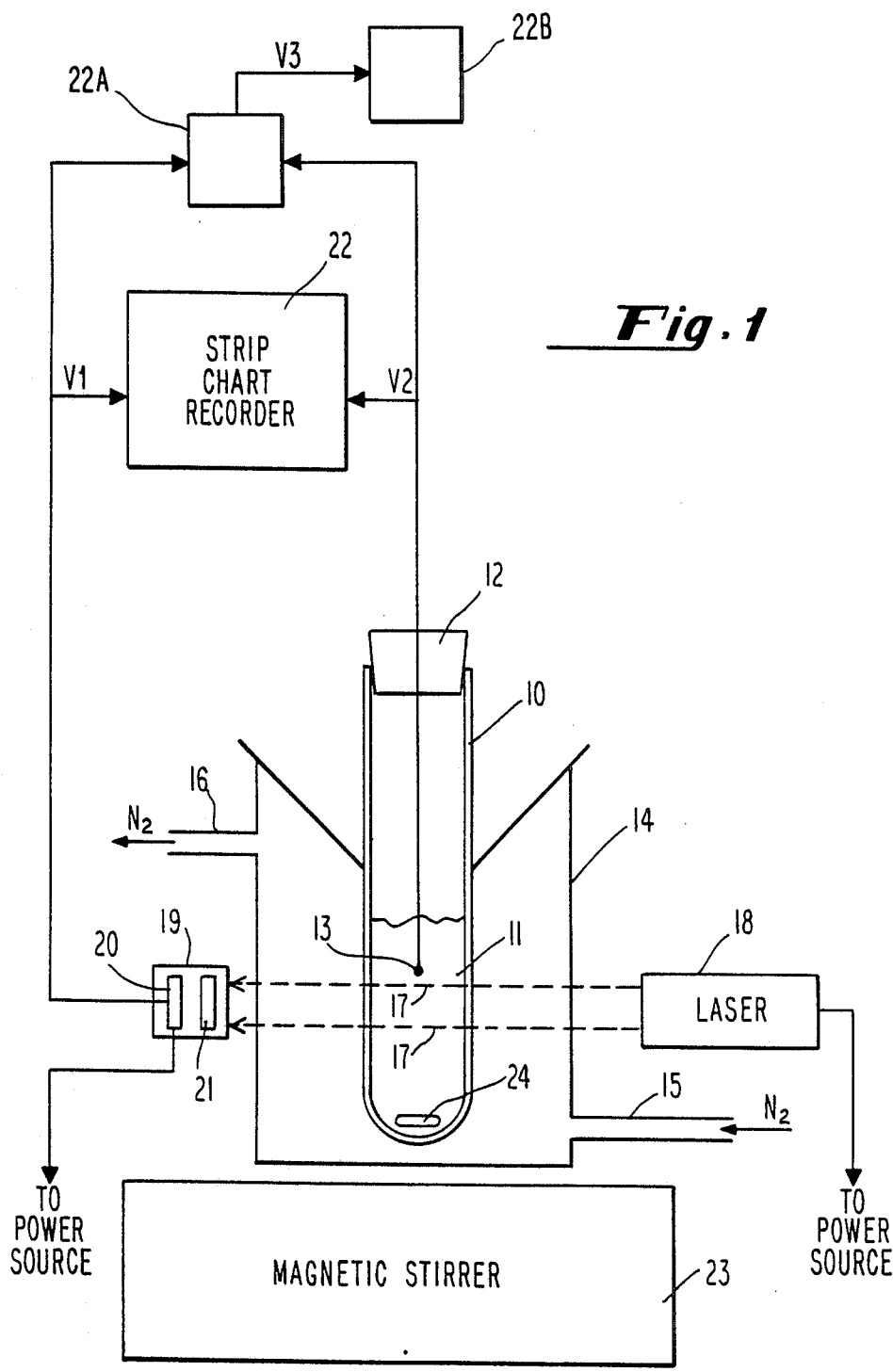
FIG. 1 is a schematic representation of an apparatus according to one embodiment of the present invention.

Referring now to FIG. 1, a double walled pyrex sample tube 10 contains the sample 11 to be tested. The space between the walls of the double walled tube 10 contains dry nitrogen at about one atmosphere pressure. The open end of the container 10 is closed by stopper 12 which contains a feed through port for thermocouple 13. The sample tube 10 is contained within a cylindrical pyrex purge shroud 14 which has an inlet 15 and an outlet 16 for the flow through of dry nitrogen as shown. The dry nitrogen thus surrounding sample tube 10 prevents any moisture condensation on the walls of the sample tube which might be encountered at subambient temperatures. Both sample tube 10 and purge shroud 14 are configured so as to provide an optical pathway through a portion of the sample. This is indicated for example, by the dotted lines labelled as 17 in FIG. 1. This optical pathway is easily and conveniently provided by constructing sample tube 10 and purge shroud 14 of a transparent material such as glass. Other means for providing an optical path through sample 11 are known in the art and are within the scope of the present invention. Light source 18 is provided as a means for projecting a highly parallel beam of monochromatic visible light along the optical pathway 17. In the preferred embodiment of the present invention, light source 18 is a source of laser light, most preferably visible laser light. Thermocouple 13 is placed within sample 11 in a position closely adjacent to but not in interference with the optical pathway 17. A photodetector 19 is placed opposite from and in alignment with light generator 18. In this way, the highly collimated light which exits the optical pathway 17 is detected by photodetector 19. Photodetector 19 comprises a photodetecting cell 20 and a light filter 21. Light filter 21 prevents the passage of ambient light by allowing the passage of substantially only that light having a wavelength equivalent to about the wavelength of the light projected by light source 18. In a preferred embodiment of the present invention, photodetecting cell 20 is a silicon photodiode and light filter 21 is a laser line filter. As is well known in the art, photodetecting cell 20 produces a voltage V1 which is related to the intensity of light striking the photodetecting cell and thermocouple 13 produces voltage V2 which is related to the temperature of the thermocouple environment. Voltages V1 and V2 are supplied to pen recorder 22. In a preferred embodiment of the present invention, pen recorder 22 is a dual-pen strip chart recorder which provides a graphical representation of the intensity of the light falling upon photodiode 20 and the temperature of the sample 11. It is preferred that apparatus according to the present invention also provide means for maintaining a uniform sample temperature wherein said means does not interfere with optical pathway 17. One such means is a magnetic stirrer which comprises a magnetic plate 23 and a stirring element 24, the operation of which is well known in the art.

It will be appreciated by those skilled in the art that the apparatus of the present invention is capable of accurately determining phase transition temperatures in a wide variety of ambient lighting conditions. This feature is provided by the provision of light filter 21 which filters out ambient light and allows the passage of only that light having a wavelength equivalent to about the wavelength of the light generated by light source 18.

Applicant has found that liquid hydrocarbon and particularly liquid hydrocarbon fuels are especially transmissive to light in the visible spectrum and that the use of a highly parallel beam of monochromatic light having a wavelength in the visible spectrum is especially useful in the determination of phase changes in these liquids. The use of light having a visible wavelength is also advantageous since it allows for easy alignment of the photodetector 19 with optical pathway 17. As the term is used herein, visible light is that light having wavelengths between about $4.0 \times 10^{-7}$ m and $7.0 \times 10^{-7}$ m. It will also be appreciated by those skilled in the art that the use of laser light in the visible spectrum with laser line filter 21 permits an apparatus which is extremely compact. This is so because a laser generator 18 which produces light having a wavelength in the visible spectrum will generally be more compact than lasers generating wavelengths in the infrared or ultraviolet region. In addition, the use of laser line filter 21 allows photocell 20 to be an extremely small and compact photodiode.

Referring once again to FIG. 1, the method of the present invention will be described according to the use of the apparatus shown therein.

A highly parallel beam of monochromatic visible light is projected along an optical pathway through sample 11 as described above. The liquid hydrocarbon sample 11 is then controlled so as to pass through the phase transition temperature. For example, if the cloud point of a hydrocarbon fuel is to be determined, the sample is initially maintained at a temperature $T_A$ which is above the cloud point. The temperature of the sample is then slowly reduced to a temperature $T_B$ which is below the cloud point of the liquid. According to one embodiment, it is preferred that the reduction in sample temperature be a substantially linear and continuous decrease without intervening temperature increases. In order to achieve the most accurate determination of the transition temperature, it is preferred that the temperature be decreased continuously and that the rate of cooling from $T_A$ to $T_B$ be no greater than about $-1°$ to $-3°$ C./min. As the temperature of sample 11 is reduced from $T_A$ to $T_B$, the intensity of the light exiting the optical pathway 17 is detected by photodetector 19 and preferably recorded. The temperature of the sample closely adjacent to the optical pathway 17 is also measured and preferably recorded. As the temperature of the sample passes from $T_A$ to $T_B$, a sharp reduction in the detected intensity of the light exiting optical pathway 17 is noted and is indicative of the occurrence of the phase transition. The temperature associated with this reduction in the intensity of the detected light is representative of the phase transition temperature of the sample.

Figure 2:
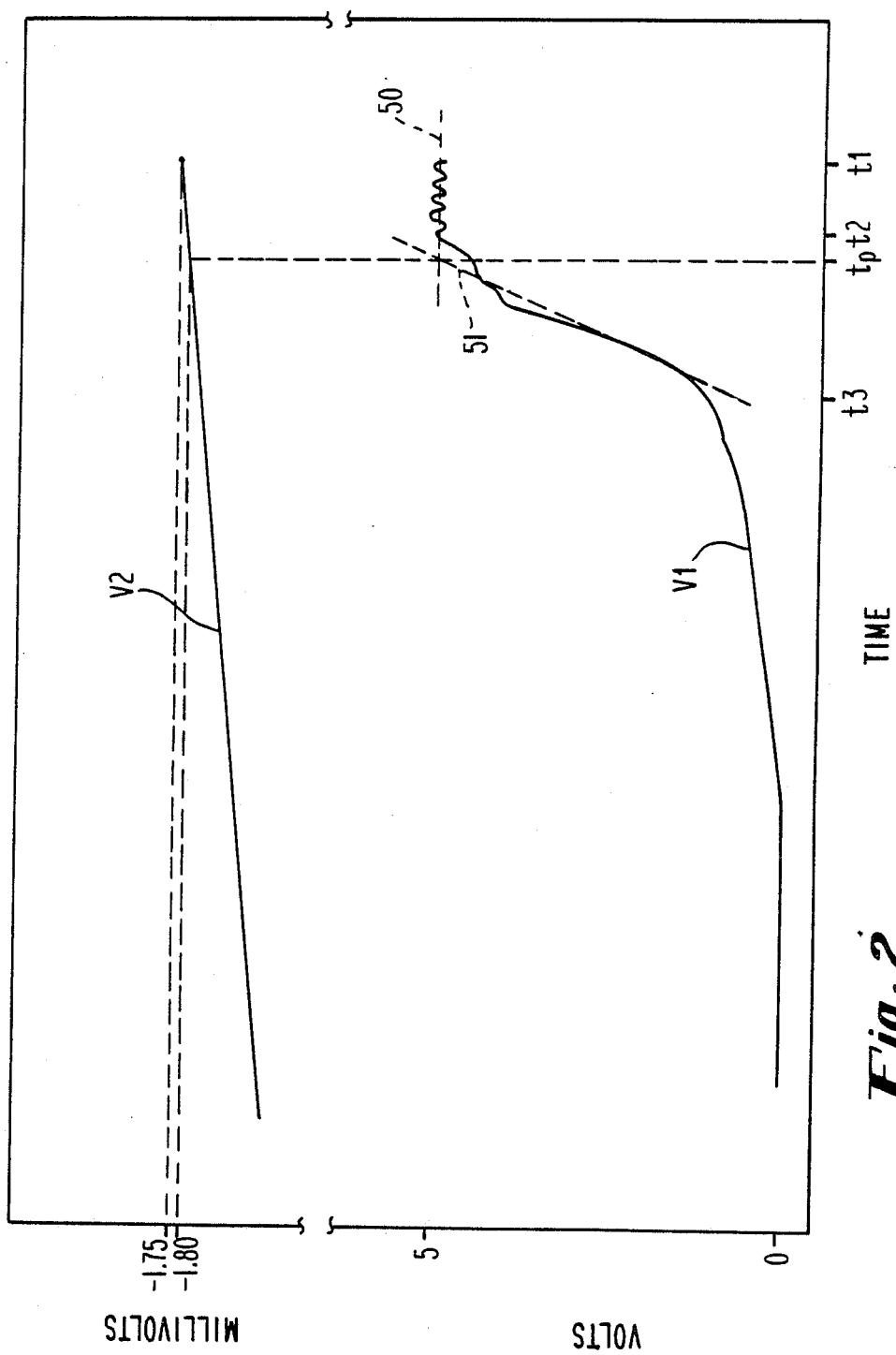
FIG. 2 shows the experimental record of light intensity and temperature for Example 1.

According to a preferred embodiment of the methods of present invention, a plurality data pairs representative of the photodiode signal V1 and the thermocouple signal V2 are generated at various preselected times during the conduction of the method. Each data pair V3 is thus representative of the light intensity and sample temperature and may be used by an analyzing means 22B to determine the transition temperature of the sample. For example, an infinite number of such data pairs are generated by the dual-pen strip chart recorder 22 which, as described above and shown in FIG. 2, records voltages V1 and V2 on a common time scale. FIG. 2 represents a strip chart record for the freezing point determination of a jet fuel in which the freezing point test started at time t1 and with a temperature $T_A$ corresponding to a thermocouple signal V2 of approximately −1.75 millivolts. At the beginning of the test, the photodiode signal V1 was about 5 volts. The temperature of the sample was controlled to move continuously downward, and eventually there was a relatively rapid drop in V1 followed by a substantially asymptotic approach to a signal level of about 0 volt. In order to aid the precise determination of the transition point of a sample material under consideration, it is convenient to break up the photodiode curve V1 into three portions. In the first portion of the test, the value of the photodiode curve oscillates in a narrow range about an average value. This portion of the curve is referred to as the "base line" and represents the transmissivity of the sample above the transition temperature. In FIG. 2, this portion of the curve is located between about t1 and t2. As the temperature of the sample approaches the transition temperature, there is a rapid drop off in the photodiode signal due to the attenuation of light caused by the phase transition. The signal from the photodiode continues decreasing rapidly and eventually approaches a final value in asymptotic fashion. While applicant does not intend to bound by or to any particular theory, the rapidly decreasing portion of the curve represents a relatively constant rate of conversion of the sample between phases. Once a major proportion of the sample has been converted, the asymptotic approach of the curve represents the conversion of the sample at a decreasing rate and therefor the signal represents an approach to the transmissivity of the solid phase. The portion of the curve between t2 and t3 in FIG. 2 roughly approximates the "rapidly decreasing" portion of the curve and the portion of the curve to the left of t3 represents the "asymptotic" portion of the curve. According to a preferred practice of the present invention, linear approximations of the "base line" and the "rapidly decreasing" portions of the curve are generated. It is most preferred that the linear approximation of the base line portion be a time independent approximation. With particular reference now to FIG. 2, horizontal line 50 is a time independent linear approximation of the base line portion of the curve and straight line 51 is a linear approximation of the rapidly decreasing portion of the curve. The intersection of the two linear approximations is then taken to be representative of the point at which the phase transition of the sample occurs. With particular reference once again to FIG. 2, the intersection of lines 50 and 51 is determined. This intersection corresponds to $t_p$ on the time scale of the strip chart. Once the intersection of lines 50 and 51 is thus established, the data pair V1, V2 most closely associated with this intersection represents to the photodiode and thermocouple voltages at the transition temperature of the sample. The sample temperature at the transition point is then determined by means well known in the art based upon thermocouple voltage V2 at that point. It will be appreciated by those skilled in the art that the above description of the techniques used in conjunction with the strip chart of FIG. 2 may be conveniently adapted for use on devices such as a computer or microprocessor, for example. That is, an electronic circuit means 22A such as a computer or microprocessor may be used to monitor voltages V1 and V2, perform the mathematical equivalents of the line approximations as described above, and then convert the voltage V2 to temperature. It will also be appreciated by those skilled in the art that it may be preferred to conduct the above described method in an iterative manner in order to more precisely determine the transition temperature. For example, the value of $t_p$ determined as described above may be used to adjust the original value of t2 chosen to represent the end of the base line portion of the curve. The new value of t2 is then used to redefine the division between the base line portion and the rapidly decreasing portion of the curve and the above described procedure is then repeated. Such iterative techniques are particularly well adapted for conduction on computer or microprocessor based systems.

According to some methods of the present invention it is preferred that a uniform temperature be maintained throughout the sample. In this way, the phase change will occur uniformly throughout the sample and the location of optical pathway 17 will not be critical. The step of maintaining such uniform temperature may be accomplished using the magnetic stirring technique described above. Other methods of maintaining such a uniform temperature are available, known in the art, and within the scope of the present invention.

An apparatus configured according to the general schematic shown in FIG. 1 was used to carry out the examples which follow. Each example is based upon an experiment in which 25 milliliters of the hydrocarbon fuel to be tested were added to sample tube 10 prior to insertion of the sample tube into the tube shroud 14. The sample tube was stoppered and immersed in a controlled temperature bath, for example dry ice or liquid nitrogen. The temperature of the sample was monitored on recorder 22. When the temperature of the sample began to approach the expected transition temperature of the sample, the sample tube 10 was removed from the bath and inserted into the purge shroud 14. Once removed from the bath, the temperature of the sample continued to decrease through the transition temperature due to the continuing but relatively slow loss of heat from the sample to the insulated sample tube 10. In this way the temperature of the sample was controlled so as to pass slowly through the transition temperature. A 0.5 milliwatt Spectra-Physics model No. 155 helium-neon laser with an output wavelength of 633 nanometers was used to project a beam of highly parallel monochromatic light through sample 11. An Oriel Corp Model No. 6533 photodiode probe was equipped with a helium neon laser line filter and was placed in alignment with the laser beam exiting the optical pathway. The laser and the photodiode were each approximately 5 centimeters from sample tube 10. An Omega type K chromel-alumel thermocouple was used to measure the sample temperature. The output signal from the photodiode and the thermocouple were fed to a dual pen strip chart recorder 22. Each sample was magnetically stirred throughout the tests.

EXAMPLE 1

The freezing point of a type A commercial jet fuel was determined using the apparatus and procedure described above. FIG. 2 is a reproduction of the dual pen strip chart recorder output which resulted from this test. As indicated by FIG. 2, the freezing point was determined to be $-46°$ C. ($-1.8$ millivolts on the type K thermocouple). The reported freezing point (ASTM D2386) on the fuel sample specification sheet which accompanied the jet fuel sample was $-47°$ C. Accordingly, the freezing point temperature determined by the methods of present invention is well within the 2.6° C. range of allowable discrepancy between different measurements at different laboratories, as specified in ASTM D2386.

EXAMPLE 2

The fluidity point of a typical No. 2 heating oil was determined using the apparatus and method described above and found to be $-13°$ C. ($-0.525$ millivolts). This value compares very favorably with the fluidity point of $-11°$ C. as measured by ASTM D2386.

EXAMPLE 3

The haze point or phase separation point of an unleaded gasoline containing about 5 volume percent methanol, 2.6 volume percent MTBE, and about 0.1 volume percent water was determined. The attenuation of the laser light and the sample temperature were measured using the apparatus and methods of the present invention as described above. While applicant does not intend to be bound by or to any theory, it is believed that attenuation of the laser light is caused by the formation of small droplets of the methanol rich phase which have become immiscible with the gasoline phase due to the lowering of the temperature of the sample. The haze point of the oxygenate/gasoline blend was determined to be 23° C. (0.90 millivolts on the type K thermocouple).

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims that follow. For example, the specification and examples are directed primarily to the measurement of phase transition temperatures which occur as a liquid hydrocarbon is cooled. It will be recognized, however, that the apparatus and methods described in the specification may be used for determining the transitions of materials other than hydrocarbons and the transitions which occur as the sample is heated rather than cooled may also be determined.

What is claimed is:

1. An apparatus operable in a plurality of ambient lighting conditions for determining the phase transition temperature of a liquid hydrocarbon fuel sample, said apparatus comprising:
   (a) a container for holding the sample and for providing an optical pathway therethrough;
   (b) a light source for projecting a highly parallel beam of monochromatic light along said optical pathway, said light having a wavelength in the visible spectrum;
   (c) means for detecting the intensity of said light exiting said optical pathway, including a detecting cell and means for allowing the passage of substantially only that light having a wavelength substantially equal to the wavelength of light from said light source; and
   (d) means for measuring the temperature of said sample as said sample passes through said transition temperature.

2. The apparatus of claim 1 further comprising means for recording the intensity of said detected light and said measured temperature.

3. The apparatus of claim 2 wherein said detecting cell comprises a photodiode and said recording means comprises a strip chart recorder connected to said photodiode and said temperature measuring means.

4. The apparatus of claim 1 wherein said light beam is a laser beam and said allowing means comprises a laser line filter.

5. The apparatus of claim 4 wherein said projecting light source is a helium-neon laser.

6. The apparatus of claim 1 further comprising means for maintaining a substantially uniform sample temperature.

7. The apparatus of claim 6 wherein said temperature measuring means comprises a thermocouple and said maintaining means comprises a jacketed sample holder equipped with a magnet stirring means.

8. The apparatus of claim 7 further comprising means for controlling the temperature of said sample to pass through said transition temperature.

9. The apparatus of claim 8 wherein said light intensity detecting means and said temperature measuring means produce signals representative of said light and said temperature.

10. The apparatus of claim 9 further comprising means for generating data pairs representative of said signals.

11. The apparatus of claim 10 wherein said means for generating data pairs comprises a dual-pen strip chart recorder.

12. The apparatus of claim 10 wherein said generating means comprises an electronic circuit means.

13. The apparatus of claim 10 further comprising means for analyzing said data pairs to determine said transition temperature.

14. The apparatus of claim 13 wherein said analyzing means comprises a microprocessor.

15. The apparatus of claim 1 further comprising means for controlling the temperature of said sample to pass through said transition temperature.

16. A method for determining the phase transition temperature of a liquid hydrocarbon sample comprising simultaneously:
   (a) projecting a highly parallel beam of monochromatic visible light from a light source along an optical pathway in said liquid hydrocarbon sample;
   (b) measuring the temperature of the liquid hydrocarbon sample;

(c) controlling the temperature of said liquid hydrocarbon sample to pass through the phase transition temperature of said sample;

(d) substantially only that light having a wavelength substantially equal to the light from said source to exit said pathway;

(e) detecting the intensity of the light exiting said optical pathway; and (f) analyzing the intensity of said detected light to determine the temperature at which the phase transition of the liquid hydrocarbon occurs.

17. The method of claim 16 further comprising the step of recording the intensity of said detected light.

18. The method of claim 16 wherein said projecting step comprises projecting a laser beam.

19. The method of claim 18 wherein said allowing step comprises interposing a laser line filter between said light source and said detecting means.

20. The method of claim 18 wherein said laser beam is generated by a helium-neon laser.

21. The method of claim 16 wherein said allowing step comprises filtering the light exiting said optical pathway.

22. The method of claim 16 further comprising the step of maintaining a uniform sample temperature.

23. The method of claim 22 wherein said maintaining step comprises magnetically stirring said sample in a jacketed sampled holder.

24. The method of claim 16 wherein said phase transition is selected from the group consisting of cloud point, fluidity point, freeze point, haze point, or water tolerance.

* * * * *